(12) United States Patent
Campbell et al.

(10) Patent No.: US 10,656,147 B2
(45) Date of Patent: May 19, 2020

(54) MAGNETIC ELEMENTS FOR PROCESSING FLUIDS

(71) Applicant: DH Technologies Development PTE Ltd., Singapore (SG)

(72) Inventors: John L. Campbell, Milton (CA); Thomas R. Covey, Richmond Hill (CA); Chang Liu, Thornhill (CA); Subhasish Purkayastha, Acton, MA (US)

(73) Assignee: DH Technologies Development Pte. Ltd. (SG)

( * ) Notice: Subject to any disclaimer, the term of this patent is extended or adjusted under 35 U.S.C. 154(b) by 562 days.

(21) Appl. No.: 15/121,803

(22) PCT Filed: Feb. 27, 2015

(86) PCT No.: PCT/IB2015/000243
§ 371 (c)(1),
(2) Date: Aug. 26, 2016

(87) PCT Pub. No.: WO2015/128725
PCT Pub. Date: Sep. 3, 2015

(65) Prior Publication Data
US 2017/0074871 A1    Mar. 16, 2017

Related U.S. Application Data

(60) Provisional application No. 61/946,364, filed on Feb. 28, 2014.

(51) Int. Cl.
*G01N 33/553*    (2006.01)
*G01N 33/543*    (2006.01)
(Continued)

(52) U.S. Cl.
CPC ... *G01N 33/54326* (2013.01); *B01F 13/0059* (2013.01); *B01F 13/0818* (2013.01);
(Continued)

(58) Field of Classification Search
USPC .......................................................... 436/526
See application file for complete search history.

(56) References Cited

U.S. PATENT DOCUMENTS 4,369,226 A * 1/1983 Rembaum ................ A61K 9/50
424/497
4,795,698 A * 1/1989 Owen .................. A61K 9/5094
252/62.56
(Continued)

FOREIGN PATENT DOCUMENTS

EP    2105202 A1    9/2009

OTHER PUBLICATIONS

International Search Report and Written Opinion for PCT/IB2015/000243 dated Jun. 10, 2015.

*Primary Examiner* — Christopher L Chin

(57) ABSTRACT

Methods and apparatus for processing fluids on a macro- or micro-scale are described. In various aspects, a fluid may have a plurality of elongated (i.e., substantially rod-shaped) magnetic elements disposed therein within a fluid container. An illustrative fluid container is an actuator electrode or a processing vial of a microfluidic device, such as a digital microfluidic device. A magnet component may be configured to generate a magnetic force sufficient to influence the movement of the plurality of elongated magnetic elements within the fluid to be processed. For example, the magnetic force (or magnetic force gradient) may influence the plurality of elongated magnetic elements to rotate, spin, and/or
(Continued)

move laterally side-to-side. The shape and movements of the plurality of elongated magnetic elements facilitate the rapid and efficient processing of the fluid, such as fluid mixing and/or fluid separation.

12 Claims, 8 Drawing Sheets

(51) Int. Cl.
*G01N 1/38* (2006.01)
*B01F 13/00* (2006.01)
*B01F 13/08* (2006.01)
*G01N 35/00* (2006.01)
*B01L 3/00* (2006.01)
*G01N 27/74* (2006.01)

(52) U.S. Cl.
CPC ..... *B01L 3/50273* (2013.01); *B01L 3/502792* (2013.01); *G01N 1/38* (2013.01); *G01N 35/0098* (2013.01); *B01L 2200/0647* (2013.01); *B01L 2300/0819* (2013.01); *B01L 2400/043* (2013.01); *B01L 2400/0427* (2013.01); *G01N 27/745* (2013.01); *G01N 2001/386* (2013.01)

(56) References Cited

U.S. PATENT DOCUMENTS

| | | | | |
|---|---|---|---|---|
| 4,978,610 | A | * | 12/1990 | Forrest ................. G01N 33/532 204/400 |
| 5,078,969 | A | | 1/1992 | Bacus |
| 7,699,979 | B2 | * | 4/2010 | Li .......................... B82Y 15/00 210/138 |
| 2004/0126903 | A1 | * | 7/2004 | Garcia ..................... B03C 1/01 436/526 |
| 2010/0124572 | A1 | | 5/2010 | Wen et al. |
| 2010/0279887 | A1 | | 11/2010 | Lee et al. |
| 2011/0070589 | A1 | * | 3/2011 | Belgrader ............... C12N 1/066 435/6.15 |
| 2011/0076670 | A1 | | 3/2011 | Boday et al. |
| 2012/0149021 | A1 | * | 6/2012 | Yung ........................ B03C 1/01 435/6.12 |
| 2018/0369831 | A1 | * | 12/2018 | Arnold ................. B03C 1/0335 |

* cited by examiner

MAGNETIC ELEMENTS FOR PROCESSING FLUIDS

RELATED APPLICATION

This application claims priority to U.S. provisional application No. 61/946,364, filed on Feb. 28, 2014, which is incorporated herein by reference in its entirety.

FIELD

The present teachings generally relate to processing fluids and, more particularly, to methods and apparatus for processing fluids on a micro- or macro-scale using magnetic elements (e.g., elongated magnetic elements).

INTRODUCTION

The use of fluids on a micro- and macro-scale has facilitated advancements in many technological fields, including ink jet printing, medical implants, sample preparation for mass spectrometers and gas chromatographs, industrial process control equipment, and lab-on--chip applications, in which biological assays and chemical analysis are performed on a microchip-sized wafer of glass, plastic, or silicon. In general, macro-scale fluid processing involves working with volumes in the milliliter range, while micro-scale fluid processing involves working with volumes of less than 1 millimeter, such as volumes in the microliter, nanoliter, and/or picoliter range.

The field of microfluidics has grown and developed to precisely and efficiently transport, mix, and analyze fluids on a micro-scale. Common fluids used in microfluidic devices include whole blood samples, bacterial cell suspensions, protein or antibody solutions, analyte solutions, and buffers. Microfluidic devices can be used alone or in combination with analytical equipment to obtain a variety of measurements concerning the microfluids or combinations thereof, including molecular diffusion coefficients, fluid viscosity, pH, chemical binding coefficients, and enzyme reaction kinetics. Other applications for microfluidic devices include capillary electrophoresis, isoelectric focusing, immunoassays, flow cytometry, sample injection of proteins for analysis via mass spectrometry, PCR amplification, DNA analysis, cell manipulation, cell separation, cell patterning, and chemical gradient formation.

Conventional or "channel-based" microfluidic systems include fluid reservoirs and networks of micron-dimensional channels. In these systems, methods to reliably merge, mix, split, and dispense the fluids are important for performance of the analysis. Typical methods and devices to aliquot a sample from a fluid reservoir through one or more channels include capillary action, valves, micro-pumps (e.g., syringe pumps, electro-osmotic pumps), and micro-pipettes.

Digital microfluidic (DMF) systems are characterized by the electrostatic manipulation of fluid droplets on open electrode arrays. When appropriate potentials are applied to these electrodes, the droplets may be driven to mix, merge, split, and/or be dispensed from fluid reservoirs. Sample and reagent droplets with volumes of less than one microliter can be moved in multiple and reconfigurable paths defined by the actuation sequence of an array of electrodes. The mechanism for fluid motion depends on a host of factors and may be due to electrowetting or dielectrophoresis. Unlike conventional microfluidics, digital microfluidics enables the transport, mixing, merging and dispensing from reservoirs of single isolated droplets. The technology has been demonstrated for diverse applications including cell based assays, enzyme assays, protein profiling, and polymerase chain reaction. Like the more common channel-based microfluidic format, DMF enjoys the benefits of low reagent consumption and fast heat transfer, and it can be easily integrated with other analytical techniques. However, DMF possesses salient features that are not present in channel-based microfluidics. In DMF, each droplet is controlled individually without the need for networks of channels, pumps, valves, or mechanical mixers. Thus, various processes can be performed simultaneously with a simple and compact design.

Magnetic particles or beads are a technology employed in microfludic systems, particularly for biochemical assays and diagnostics, such as disclosed in an article entitled "Magnetic bead handling on-chip: new opportunities for analytical applications," authored by Martin A. M. Gijs and published in Microfluid Nanofluid (2004; I: 22-40). Magnetic particle technology is indeed a robust technology that provides for high performance (e.g., device sensitivity and accuracy) and also provides for easy automation of assay protocols. For many applications, the surface of magnetic particles is coated with a suitable ligand or receptor, such as antibodies, lectins, oligonucleotides, or other bioreactive molecules, which can selectively bind a target substance in a mixture with other substances. One key element in magnetic particles bio-separation and handling technology is efficient mixing to enhance the reaction rate between the target substances and the particle surfaces. However, conventional mass transfer within a microfluid droplet is a function of molecular diffusion, resulting in long mixing times. Indeed, as for any surface-based assay, the reaction is strongly limited by the natural diffusion process. Thus, strong steering and mixing is necessary to promote the affinity binding reaction between the ligand and the target substance.

Conventional sample mixing methods include sonication and mechanical agitation of the sample fluid. However, these have not proven effective at the micro-scale, particularly for DMF devices. For microfluid systems using magnetic particles, previous techniques have employed moving a magnet relative to a stationary container or movement of the container relative to a stationary magnet using mechanical means, thereby inducing a "relative displacement" of the magnetic gradient position within the container. This magnetic field gradient displacement may induce the magnetic particles to move continuously with the change of the magnet (i.e., magnetic field gradient) position, thereby effecting mixing. However, with this method the magnetic field gradient may attract and confine the particles in a cavity region close to the walls of the container. In such a condition, the contact between the particles and the test medium is limited to the cavity space, which greatly reduces mixing efficiency. In addition, with spherical or bead-shaped magnetic particles, mechanical and/or magnetic agitation may cause the magnetic particles to aggregate and cluster in discrete areas within a sample container or surface of a microfluid system. As such, the magnetic particles would not be capable of facilitating sample mixing or separation because their movement and exposure to the sample volume becomes highly limited.

Accordingly, a need exists to improve the overall speed and efficiency of sample mixing and separation within micro- and macro-fluidic environments using magnetic particles, including ultra-fast homogenous mixing of sample fluids, thereby allowing much more sample volume to be effectively and rapidly contacted with particle surfaces.

SUMMARY

Apparatus, systems, and methods in accordance with the applicant's present teachings allow for the processing of fluids on the macro- or micro-scale. The fluids are processed using magnetic elements (e.g., elongated, substantially rod-shaped magnetic elements) arranged with the fluid or mixture of fluids. The movement of the elongated magnetic elements may be influenced by a magnetic field generated by a magnet component. For instance, the elongated magnetic elements may be influenced to rotate, spin, and/or move laterally side-to-side within the fluid. The movement of the elongated magnetic elements within the fluid may operate to rapidly and efficiently mix the fluid and/or capture target analytes within the fluid.

In one aspect, a fluid processing system is described that may include a fluid container having a plurality of elongated magnetic elements arranged therein, the fluid container being configured to receive at least one fluid. The fluid processing system may further include a magnet component configured to generate a magnetic field within the fluid container sufficient to magnetically influence the plurality of elongated magnetic elements. A control component (herein also referred to as a controller) coupled to the magnet component can control the magnetic field applied by the magnet component to the elongated magnetic elements to control movement thereof. In some aspects, the system is configured such that the movement of the elongated magnetic elements causes mixing of the at least one fluid. In some aspects, the system is configured to process the at least one fluid by performing fluid separation to capture at least one target analyte within the at least one fluid.

In some aspects, the elongated magnetic elements may include a magnetic core and a non-magnetic coating. The magnetic core may include at least one of $Fe_2O_3$ and $Fe_3O_4$. The magnetic core may be coated with a non-magnetic coating. In an aspect, the magnetic core may be coated with a silicon material (e.g., $SiO_2$). In an aspect, the elongated magnetic elements may have a longitudinal length of about 1 μm to about 10 μm. In an aspect, the magnetic elements have a diameter of about 1 μm to about 5 μm.

In various aspects, the fluid processing system may be formed as a microfluidic device. In some aspects, the microfluidic device may be a digital microfluidic device (DMF). The fluid container may include various types of fluid reservoirs, actuator electrodes, processing vials, or the like. In some aspects, the fluid processing device may be configured to process fluid at the macro-scale, including processing at least 1 microliter of the fluid.

In some aspects, the magnet component may be configured to generate a three-dimensional rotating magnetic force within a fluid container. In some aspects, the magnet component may be configured to generate a magnetic field gradient within a fluid container. In an aspect, the magnetic field is configured to influence the plurality of elongated magnetic elements to rotate within a fluid. In an aspect, the magnetic field is configured to influence the plurality of elongated magnetic elements to move laterally from side-to-side within a fluid.

In some aspects, the fluid processing system may be configured to process the fluid for various analyses, including mass spectrometry, gas chromatography, immunoassays, biological assays, chemical analysis, and/or chemical production. In some aspects, the elongated magnetic elements may be coated with an affinity material having an affinity for a target analyte within the fluid. In this manner, the fluid processing system may perform fluid separation on the fluid to capture an analyte of interest and/or to cause a biological and/or chemical reaction.

In accordance with various aspects of the applicant's present teachings a digital microfluidic device is described that may include a plurality of fluid containers comprising at least one fluid reservoir and an array of actuating electrodes, the plurality of fluid containers being configured to store at least one fluid, a plurality of elongated magnetic elements arranged within at least one of the plurality of fluid containers, a magnet component configured to generate a magnetic field within the at least one of the plurality of fluid containers having the plurality of elongated magnetic elements arranged therein sufficient to magnetically influence the plurality of elongated magnetic elements, and a controller coupled to the plurality of fluid containers and the magnet component. The controller may be configured to apply a voltage to the array of actuating electrodes to deposit a volume of the at least one fluid on one of the plurality of fluid containers, apply a voltage to the array of actuating electrodes to move the volume of the at least one fluid to the at least one of the plurality of fluid containers having the plurality of elongated magnetic elements arranged therein, and control the magnetic field generated by the magnet component to process the unit of the at least one fluid.

In various aspects, a method for processing a fluid may include arranging a plurality of elongated magnetic elements within a fluid container and configuring a magnet component to generate a magnetic field within the fluid container. A fluid may be received at the fluid container and a magnet component may be activated to generate a magnetic field within the fluid container sufficient to magnetically influence the plurality of elongated magnetic elements, thereby processing the at least one fluid.

In accordance with various aspects of the applicant's present teachings, a magnetic composition may include a plurality of magnetic elements having a magnetically susceptible core and a non-magnetic coating, the plurality of magnetic elements having at least one cross-sectional dimension in a range from about 1 μm to about 10 μm. By way of example, a magnetic composition may include a plurality of elongated magnetic elements having a magnetically susceptible core and a non-magnetic coating, the plurality of elongated magnetic elements being substantially rod-shaped and having a longitudinal length of about 1 μm to about 10 μm.

BRIEF DESCRIPTION OF THE DRAWINGS

A detailed description of various embodiments is provided herein below with reference, by way of example, to the following drawings. It will be understood that the drawings are exemplary only and that all reference to the drawings is made for the purpose of illustration only, and is not intended to limit the scope of the embodiments described herein below in any way. For convenience, reference numerals may also be repeated (with or without an offset) throughout the figures to indicate analogous components or features.

DETAILED DESCRIPTION

Figure 1A:
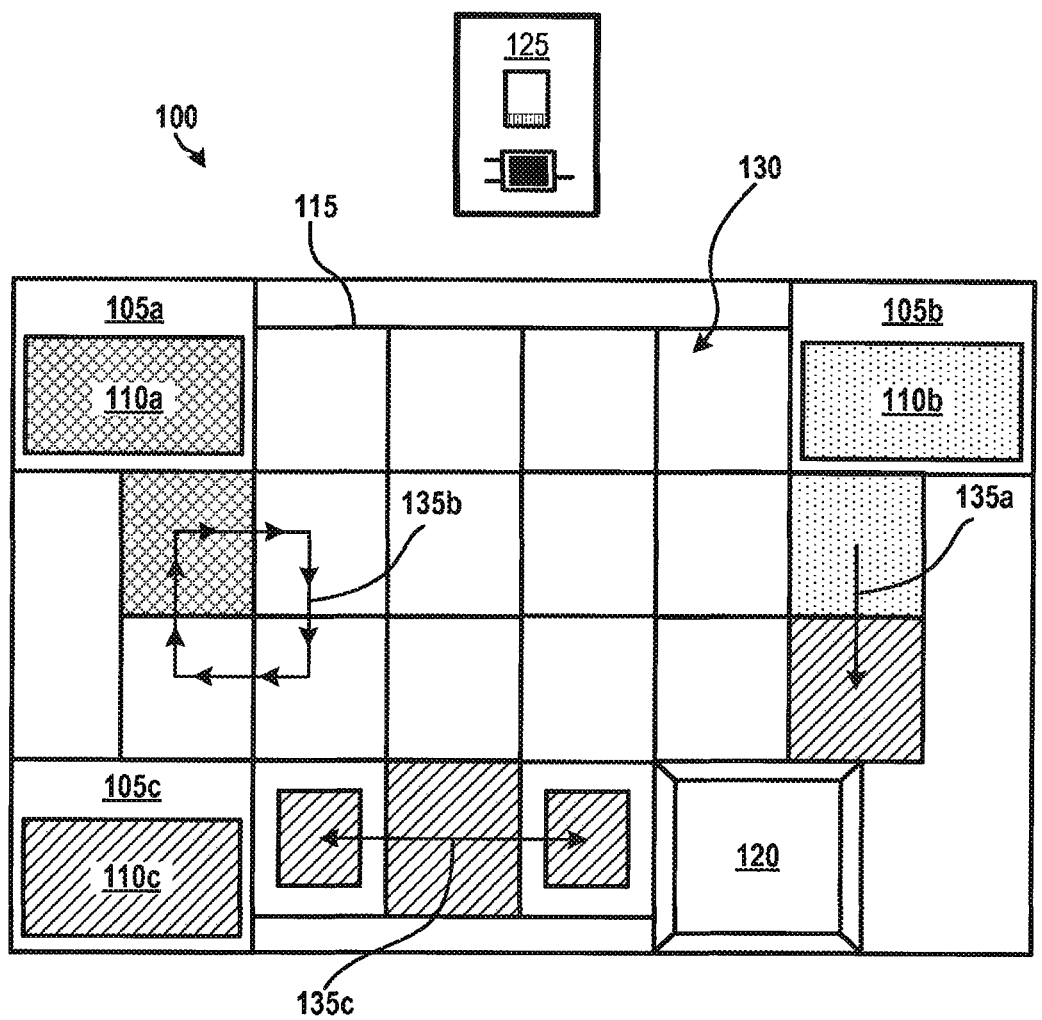
FIG. 1A, in schematic diagram, depicts a top view of a microfluidic device according to various aspects of the applicant's teachings.

Those skilled in the art will understand that the methods, systems, and apparatus described herein are non-limiting exemplary embodiments and that the scope of the applicant's disclosure is defined solely by the claims. While the applicant's teachings are described in conjunction with various embodiments, it is not intended that the applicants' teachings be limited to such embodiments. On the contrary, the applicant's teachings encompass various alternatives, modifications, and equivalents, as will be appreciated by those of skill in the art. The features illustrated or described in connection with one exemplary embodiment may be combined with the features of other embodiments. Such modifications and variations are intended to be included within the scope of the applicants' disclosure. Various terms are used herein consistent with their customary meanings in the art. The term "about" as used herein indicates a variation of less than 10%, or less than 5%, or less than 2%.

The present teachings generally relate to fluid processing systems configured to mix, separate, suspend, filter, or otherwise process fluids. In various aspects, fluid processing systems may be configured to process fluids at the macro- or micro-scale. In general, the macro-scale involves fluid volumes in the millimeter range, while the micro-scale involves fluid volumes below the milliliter range, such as microliters, picoliters, or nanoliters. However, it will be appreciated in light of the present teachings that the fluid processing systems may process any fluid volume suitable for use in embodiments described herein. In various aspects, the fluid processing systems may use elongated (e.g., rod-shaped or substantially rod-shaped) magnetic elements to process fluids. The elongated magnetic elements may be arranged within a fluid and may be subjected to magnetic forces configured to facilitate the movement of the elongated magnetic elements within the fluid. In various aspects, a magnet component may be configured to generate the magnetic forces. In some aspects, the magnet component may include one or more magnetic lenses. In some aspects, the magnetic force may include a three-dimensional (3D) rotating magnetic field. In various aspects, the magnetic forces may be configured to influence the elongated magnetic elements to move within the fluid in a rotating or spinning motion and/or in a lateral side-to-side motion.

The use of elongated magnetic elements, for instance, as compared to magnetic beads, provides multiple technological advantages. One non-limiting example of a technological advantage includes providing a larger surface-to-volume ratio for increased sample contact, for example, to improve analyte capture efficiency in a magnetic immunoassay. Another non-limiting example of a technological advantage includes increased sample mixing efficiency as the elongated magnetic elements may operate as a population of magnetic stir bars, providing for increased sample mixing efficiency. It will be appreciated in light of the present teachings that the fluid processing systems described herein provide multiple other technological advantages in addition to the aforementioned non-limiting examples.

While the systems, devices, and methods described herein can be used in conjunction with many different fluid processing systems, an exemplary digital microfluidic system 100 for such use is illustrated schematically in FIG. 1A. It should be understood that the digital microfluidic system 100 represents only one possible fluid processing system for use in accordance with embodiments of the systems, devices, and methods described herein, and fluid processing systems having other configurations and operational characteristics can all be used in accordance with the systems, devices and methods described herein as well.

FIG. 1A depicts a top view of a microfluidic device 100 which may be used, for example, for droplet-based assays, such as cell culture and cell assays using digital microfluidics. The microfluidic system 100 may include reservoir electrodes 105a-c configured to contain various fluids 110a-c, including, without limitation, reagents, buffers, solvents, magnetic beads, elongated magnetic elements, biological samples (e.g., cells), chemical samples, dyes, wash solutions, and any other fluid capable of operating according to the present teachings described herein. The fluids 110a-c may be dispensed onto a fluid surface 130 of actuating electrodes 115 adjacent by applying voltages to the electrodes 115 and to the reservoir electrodes 105a-c. In some embodiments, a single droplet of a fluid 110a-c may be dispensed onto the fluid surface 130. In some embodiments, a single droplet of a fluid 110a-c may have a volume in the picoliter to microliter range, e.g., about 150 nanoliters (nL) of fluid.

The fluid surface 130 may include arrays of actuating electrodes 115. Although FIG. 1 depicts multiple actuating electrodes 115, only one is labeled in FIG. 1 to simplify the figure. Voltages may be applied to the actuating electrodes 115 to move the fluids 110a-c around the fluid surface 130. For instance, the fluids 110a-c may be moved from one electrode 115 to another electrode. Other movements, such as combining fluids 135a, fluid mixing 135b, and fluid splitting 135c, may be carried out through actuation of various electrodes 115 and sequences and/or combinations thereof.

The electrodes 105a-c, 115 may be deposited on the fluid surface 130 and subsequently coated with a layer of a hydrophobic insulator, such as Teflon® AF or Cytop®. The reservoir electrodes 105a-c may be configured to hold multiple units (i.e., droplets) of fluid 110a-c, while the actuating electrodes 115 may be configured to hold less units of fluid 110a-c, such as one to three droplets. In some embodiments, electrical contact pads (not shown) may be connected to the electrodes 105a-c, 115 to enable the electrodes 105a-c, 115 to be individually addressed or actuated. The electrodes 105a-c, 115 may be formed from various materials, including copper, gold, platinum, chromium, and combinations thereof.

In some embodiments, the microfluidic device 100 may further include a controller 125 that is in electrical communication with the reservoir electrodes 105*a-c*, actuating electrodes 115, and/or other components of the microfluidic device 100, such as one or more power supplies (not shown) for applying apply voltages to the electrodes. In some embodiments, for example, the controller 125 can provide control signals to the power supplies to coordinate the motion of fluids 110*a-c* on the fluid surface 130.

The controller 32 can be implemented using known electrical components, such as suitable integrated circuits, and known engineering methods. For example, the controller 32 can include one or more processors, memory modules, communication modules for communicating with the detector 114, the power supplies, and other components of the microfluidic device system 100 as well as software instructions for implementing the present teachings. In some embodiments, the controller 32 can further comprise one or more buffers and signal processing components that can facilitate the analysis of signals received from the detector 114.

The manipulation of fluids 110*a-c* on the fluid surface 130 may be at the unit, droplet, or micro-scale range. In some embodiments, the microfluidic device 100 may include a fluid reservoir or vial 120 (e.g., a "processing vial") configured to contain fluids 110*a-c* at the macro- or micro-scale. In some embodiments, the processing vial 120 may be configured to contain at least about 1 milliliter (mL) of fluid 110*a-c*. In some embodiments, the processing vial 120 may be configured to contain a volume of fluid 110*a-c* ranging from one unit to about 1 mL of fluid 110*a-c*. In some embodiments, the processing vial 120 may be configured to contain a volume of fluid 110*a-c* greater than about 1 mL of fluid 110*a-c*. The fluid reservoirs 105*a*-105*c*, electrodes 115, and processing vial 120 may separately and collectively be referred to as "fluid containers" herein. The volume of fluid 110*a-c* within the processing vial 120 may be obtained by dispensing multiple droplets of the fluid 110*a-c* into the processing vial 120.

Figure 1B:
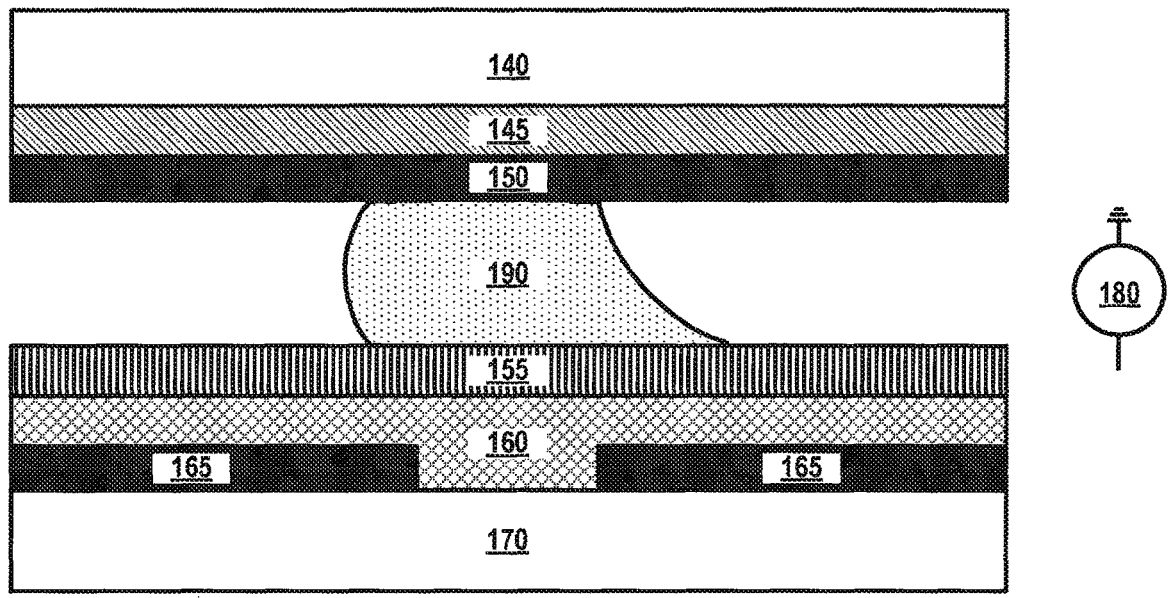
FIG. 1B, in schematic diagram, depicts a cross-sectional view of a microfluidic device in a two-plate (closed) configuration according to various aspects of the applicant's teachings.

The microfluidic device 100 may be configured in a two-plate (closed) configuration or a one-plate (open) configuration. FIG. 1B depicts a cross-sectional view of the microfluidic device 100 in a two-plate (closed) configuration according to various aspects of the applicant's teachings. As shown in FIG. 1B, electrodes 165 may be arranged on a substrate layer 170 and may be separated from each other by a dielectric material 160 (e.g., parylene-C). In some embodiments, the microfluidic device 100 can have more than one dielectric layer 160. Located on top of dielectric material 160 is a hydrophobic layer 155 (e.g., Teflon®, Cytop®, or the like). Spaced above the electrodes 165 and dielectric layer 160 is a continuous reference electrode 145 coated on a substrate layer 140. A hydrophobic layer 150 may be coated on reference electrode 145.

Liquid droplets 190 may be arranged between hydrophobic layers 150 and 155. Electrodes 165, voltage source 180, and the continuous reference electrode 145 together form an electric field, which may be digitally manipulated by the controller 125. For droplet 190 manipulation, reference electrodes 145 may be biased to a potential different from the actuating potential. In some embodiments, the reference potential is ground.

Figure 1C:
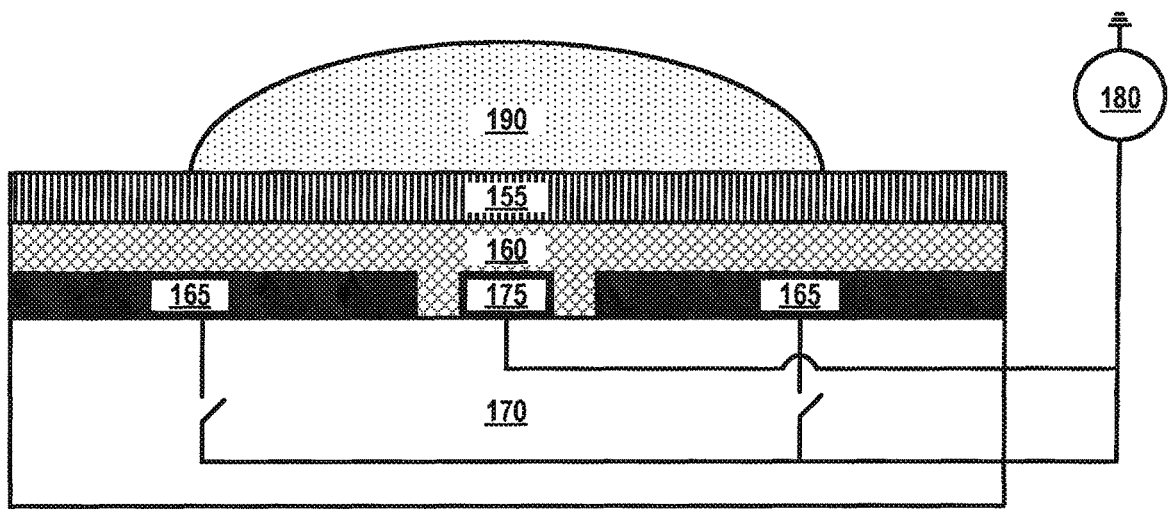
FIG. 1C, in schematic diagram, depicts a cross-sectional view of a microfluidic device in a one-plate (open) configuration according to various aspects of the applicant's teachings.

FIG. 1C depicts a cross-sectional view of the microfluidic device 100 in a one-plate (open) configuration according to various aspects of the applicant's teachings. In FIG. 1C, layers 140, 145, and 150 of FIG. 1B have been removed from the microfluidic device 100. Rather than having a dedicated reference electrode layer 145, the reference electrode in the one-plate (open) configuration is patterned adjacent to electrodes 165, forming a continuous grid 175 separated from electrodes 165 by the dielectric material 160. The continuous grid 175 extends in both directions defining the plane in which electrodes 165 are located. Reference electrodes can also be coplanar with the top surface of the dielectric layer. The reference electrodes in the one-plate (open) configuration are not limited to the continuous grid 175 depicted in FIG. 1C, as this is for illustrative purposes only. Indeed, the reference electrodes may be configured as a wire, array of electrodes, or any other form capable of operating according to applicant's teachings.

Figure 2:
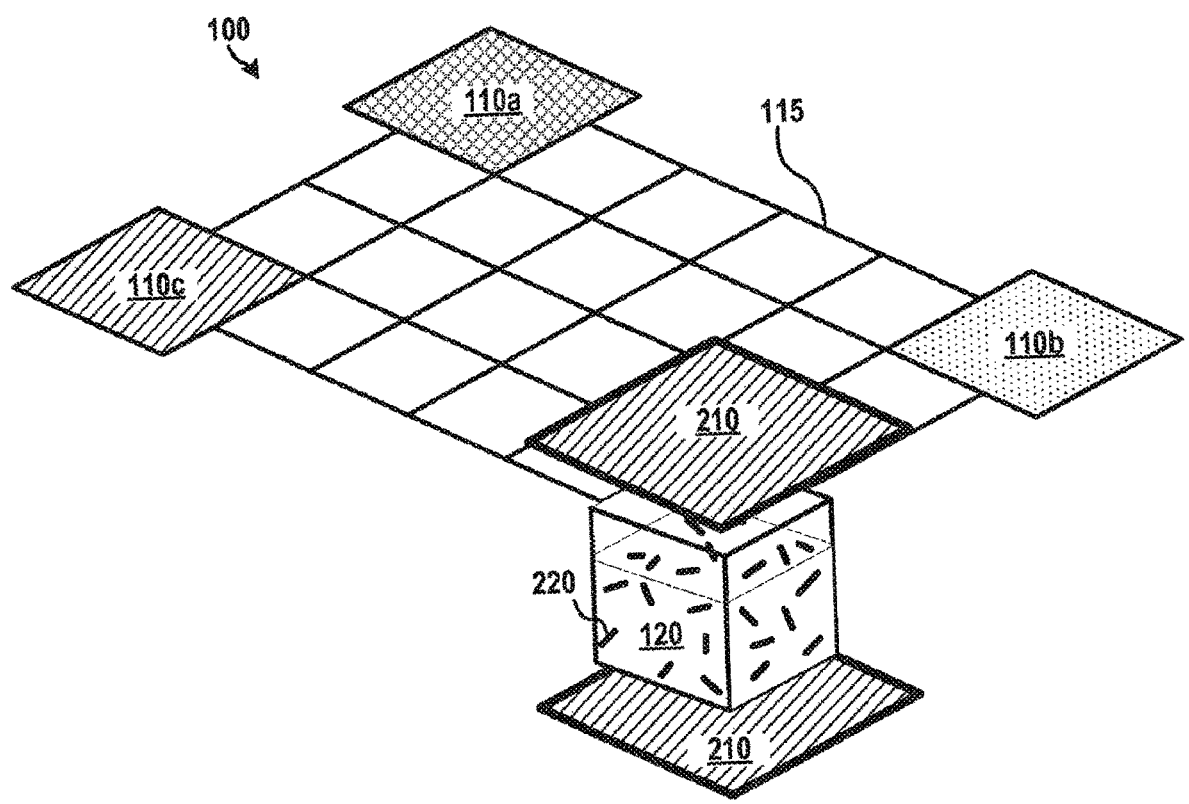
FIG. 2, in schematic diagram, depicts a microfluidic device according to various aspects of the applicant's teachings.

FIG. 2 depicts a microfluidic device according to various aspects of the applicant's teachings. As shown in FIG. 2, the microfluidic device 100 may include a processing vial 120 configured to receive various fluids 110*a*-110*c*. The processing vial 120 may contain elongated magnetic elements 220 arranged therein. The elongated magnetic elements 220 or portions thereof may be formed from various magnetically susceptible materials, including, without limitation ferromagnetic materials, such as various iron oxide materials (e.g., $Fe_2O_3$, $SiO_2$ coated $Fe_2O_3$, $Fe_3O_4$, or the like), magnetic polymers, Co—Mn compounds, and Ni-doped ZnO. In some embodiments, the magnetic elements 220 may include a magnetic "core" coated with a non-magnetic coating, for example, configured to not react with the fluids 110*a-c* and/or to selectively bind a material (e.g., a biomaterial) of interest.

The elongated magnetic elements 220 will generally be rod-shaped and may have various sizes, for instance, according to the particular application and/or characteristics of the microfluidic device 100. For example, the elongated magnetic elements 220 may have a diameter of about 1 µm to about 5 µm and a length of about 3 µm to about 10 µm. In another example, the elongated magnetic elements 220 may have a diameter of about 5 nm to about 100 nm and a length of about 10 nm to about 500 nm. The concentration and/or number of elongated magnetic elements 220 may be configured based on the characteristics of the fluids 110*a-c* and/or the particular application. For instance, the number of elongated magnetic elements 220 within a fluid 110*a-c* may comprise about 1% to about 5% per volume of the fluid 110*a-c*. By way of non-limiting example, the concentration of the magnetic elements 220 within the fluid 110*a-c* can be in a range between about $1 \times 10^3$ particles/mL to about $1 \times 10^{10}$ particles/mL, for example, about $3 \times 10^8$ particles/mL. For example, the concentration of the magnetic elements 220 within the fluid 110*a-c* can be selected to enable the efficient capture of target analytes, as otherwise discussed herein. In some embodiments, the elongated magnetic elements 220 may have a magnetic susceptibility ($X_m$) of about 1 to about 10.

The microfluidic device 100 may further include a magnet component 210 configured to generate a magnetic force sufficient to influence the movement of the elongated magnetic elements 220. In some embodiments, the magnet component 210 may include an assembly of magnets that are positioned around the microfluidic device 100 and/or processing vial 120 such that the magnet components 210 can be selectively activated. By way of example, a plurality of magnet components 210 can be radially positioned Alternatively or additionally, in some embodiments, the magnet component 210 may be coupled to the controller 125 and/or other magnetic control device (e.g., a magnetic controller) (not shown) capable of providing automated control and/or movement of the magnet component 210. For example, the magnet component 210 may be coupled to a motor configured to move the magnet component 210 in various positions around the microfluidic device 100 and/or the processing vial 120. In another example, the magnet component 210 may include an assembly of magnets with a first portion of the assembly of magnets radially positioned at or substantially at a top portion of the microfluidic device 100 and/or processing vial 120 and a second portion of the assembly of magnets radially positioned at or substantially at a bottom portion of the microfluidic device 100 and/or processing vial 120. In various embodiments, the magnet component 210 may include a neodymium magnet (e.g., NdFeB). In some embodiments, the magnet component 210 may include permanent magnets, coils, magnetic bars, magnetic cylinders, and/or combinations thereof. In some embodiments, the magnet component 210 may be configured to produce a magnetic induction of about 0.5 Tesla to about 2 Tesla.

Figure 3A:
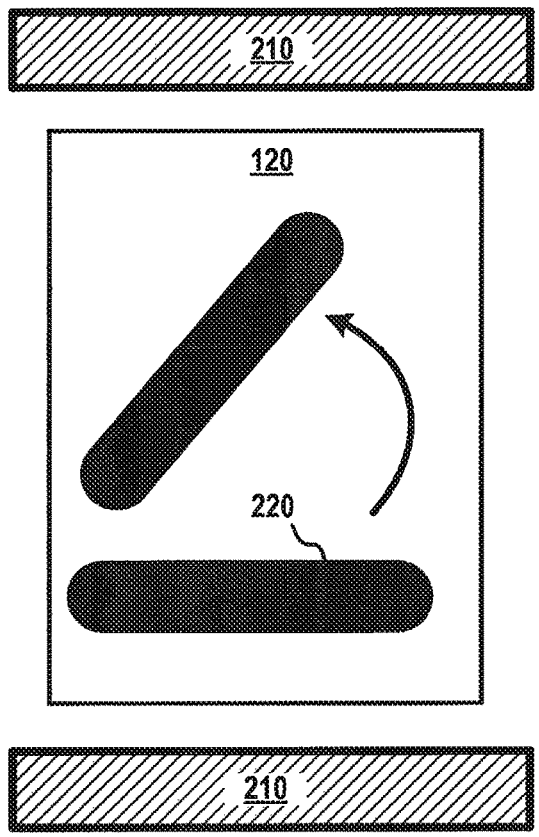
FIGS. 3A and 3B depict illustrative movements of elongated magnetic elements according to various aspects of the applicant's teachings.
Figure 3B:
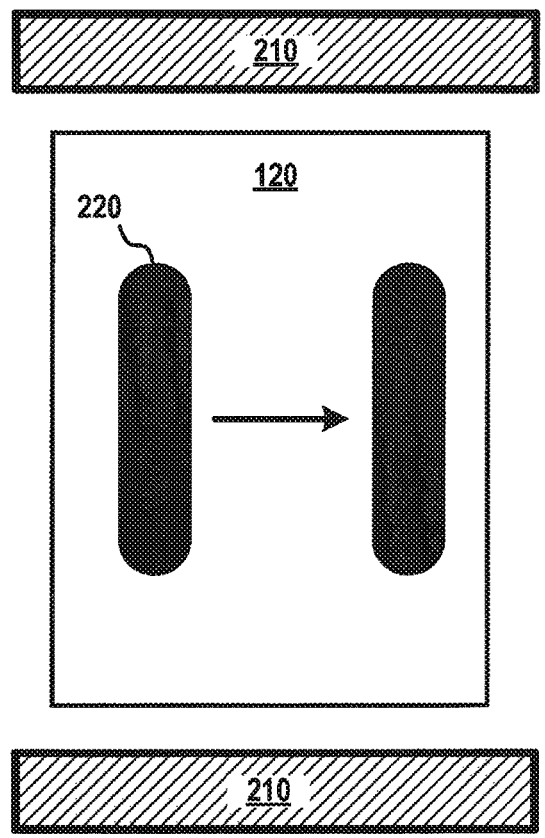

The magnet component 210 may be configured to provide a magnetic force that generates a magnetic field gradient. In this manner, the magnet component 210 may generate a magnetic force that influences the movement of the elongated magnetic elements 220. Referring to FIG. 3A, the magnet component 210 may be configured to generate a magnetic force that causes the elongated magnet components 220 to spin, rotate, partially rotate, or rotate in a substantially circular plane. As shown in FIG. 3B, the magnet component 210 may be configured to generate a magnetic force that causes the elongated magnetic elements 220 to move in a lateral side-to-side motion. The elongated magnetic components 220 are not limited to rotational motion or lateral side-to-side motion, as the magnet component 210 may be configured to generate magnetic fields, including dynamically changing magnetic fields, capable of influencing any type of motion in the elongated magnetic elements 220 capable of operating according to some embodiments. In order to influence the movement of the elongated magnetic elements 220 in a particular direction, the magnet component 210 and/or portions thereof may be actuated, de-activated, moved with respect to the processing vial 120 and/or microfluidic device 100, or a combination thereof. For instance, the magnet component 210 may be configured to generate a three-dimensional magnetic field, including, for example, a three-dimensional rotating magnetic field. In some embodiments, the processing vial 120 may include non-elongated magnetic elements having a different size, shape, and/or magnetic properties than the elongated magnetic elements 220, including magnetic beads or particles of other shapes. In such embodiments, the three-dimensional magnetic field may be used to differentially influence or drive the non-elongated magnetic elements, for instance, to enhance mixing efficiency within the processing vial 120.

In some embodiments, the magnet component 210 may be configured to generate a magnetic field that influences the motion of the magnetic particles (e.g., the elongated magnetic elements 220) arranged in a processing vial 120 so as to spin, rotate or otherwise move the magnetic particles in an orbit or path in and out of the influence of the magnetic field. In such an embodiment, the magnetic component 210 may include multiple magnets equidistantly aligned at spatially fixed positions, for example, from an area through which the spinning or rotating processing vial may 120 may pass through and be subject to the influence of the magnetic field. In some embodiments, the radial positions of the multiple magnets of the magnetic component 210 may alternatingly deviate by a slight positive and negative offset from the mean orbit or path of the processing vial 120 to periodically influence the elongated magnet components 220 inbound and outbound during rotation around the orbit or movement along the path. In such an embodiment, advection may be induced by the relative motion of the elongated magnet components 220 with respect to the fluids 110a-c, resulting from the magnetic and centrifugal forces, as well as inertia.

Figure 4A:
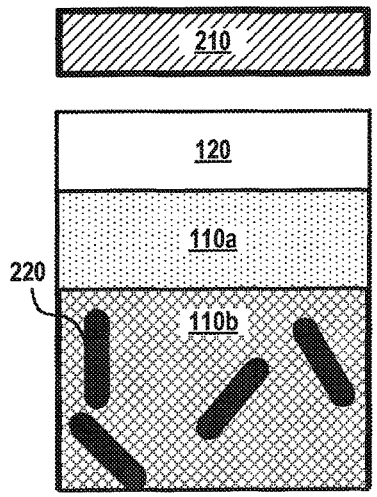
FIGS. 4A-D depict an illustrative flow diagram for mixing a fluid according to various aspects of the applicant's teachings.
Figure 4B:
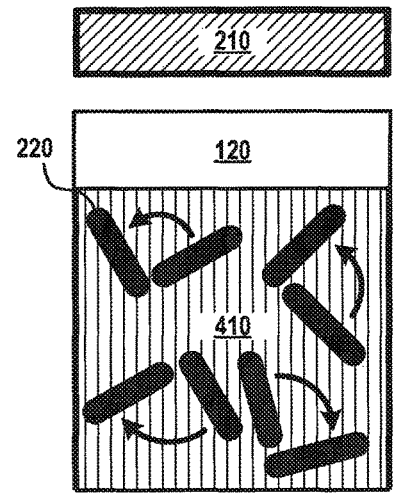
Figure 4C:
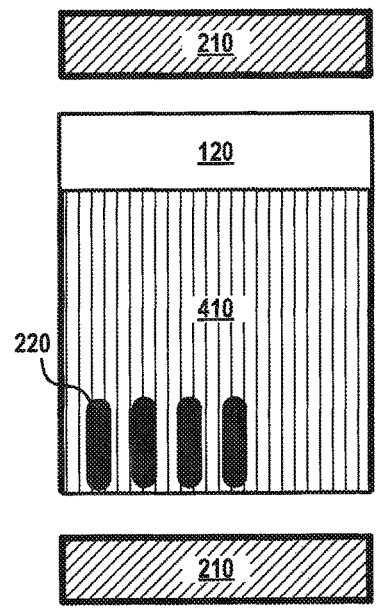
Figure 4D:
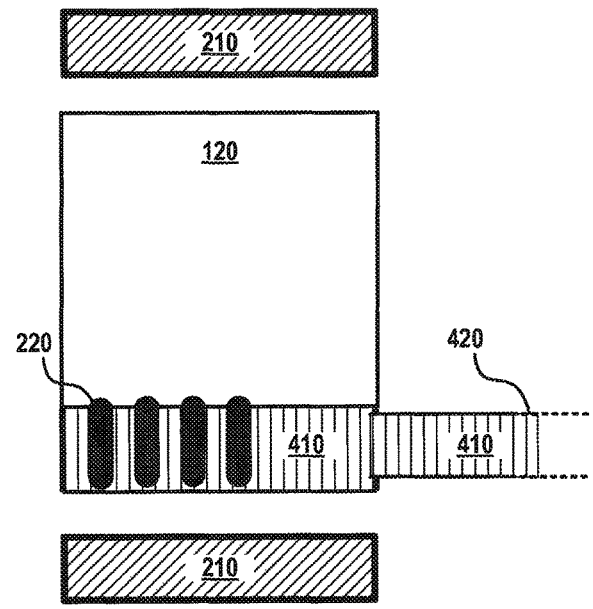

FIGS. 4A-D depict an illustrative flow diagram for mixing a fluid according to various aspects of the applicant's teachings. In FIG. 4A, fluid 110a and fluid 110b are combined within the processing vial 120, which contains elongated magnetic elements 220. In FIG. 4B, the magnet component 210 is activated, for example, to generate a magnetic force that causes the elongated magnetic elements 220 to rotate or spin. The rotation of the elongated magnetic elements 220 facilitates the rapid and complete mixing of fluid 110a and fluid 110b to form fluid 410 (the mixture of fluid 110a and fluid 110b). In some embodiments, the microfluidic device 100 may mix a 1 milliliter sample in about 5 seconds to about 10 seconds. As shown in FIG. 4C, the magnetic force generated by the magnet component 210 may be changed from a magnetic force that causes the elongated magnetic elements 220 to rotate to a magnetic force that immobilizes the elongated magnetic elements 220 within the processing vial 120. In this manner, the fluid 410 may be removed from the processing vial 120, for example, through a drain channel 420, without removing the elongated magnetic elements 220, as depicted in FIG. 4D. Alternatively, a magnetic force may be generated by the magnetic component 220 to influence the elongated magnetic elements 220 to move out of the processing vial 120, for example, and onto a surface such as a fluid surface 130 of actuating electrodes 115. In this manner, only the fluid 410 (or substantially all of the fluid 410) in the processing vial 120.

Figure 5A:
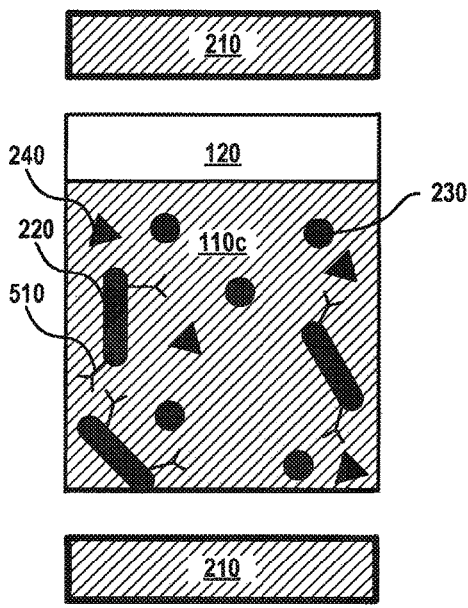
FIGS. 5A-D depict an illustrative flow diagram for fluid separation according to various aspects of the applicant's teachings.
Figure 5B:
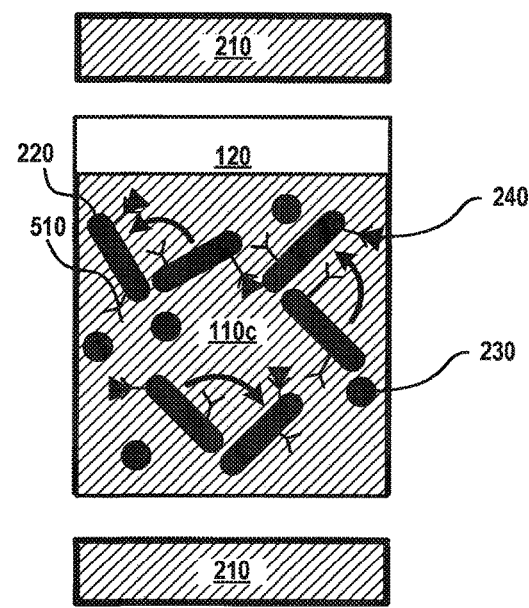
Figure 5C:
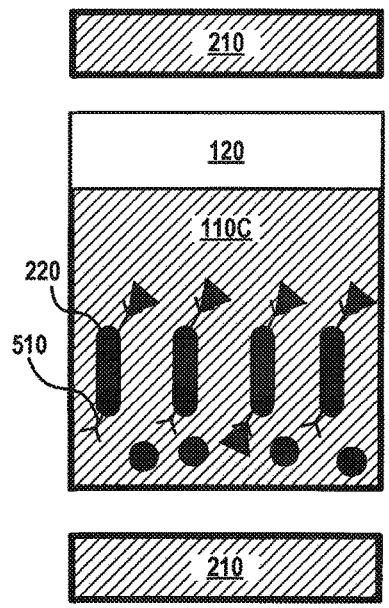

FIGS. 5A-D depict an illustrative flow diagram for fluid separation according to various aspects of the applicant's teachings. As shown in FIG. 5A, a fluid 110c containing various analytes 230, 240 may be dispensed into the processing vial 120 containing elongated magnetic elements 220 having an affinity for one of the analytes. In some embodiments, the analytes 230, 240 may be antigens, antibodies, proteins, or other biological analytes. For instance, the elongated magnetic elements 220 may be coated with an affinity material (e.g., antibodies) 510 having an affinity for a target analyte 240. In FIG. 5B, the magnet component 210 may be activated to generate a magnetic force that causes the elongated magnetic elements 220 to rotate or spin, thereby facilitating rapid and efficient contact between the antibodies 510 arranged on the elongated magnetic elements 220 and the target analyte 240.

Figure 5D:
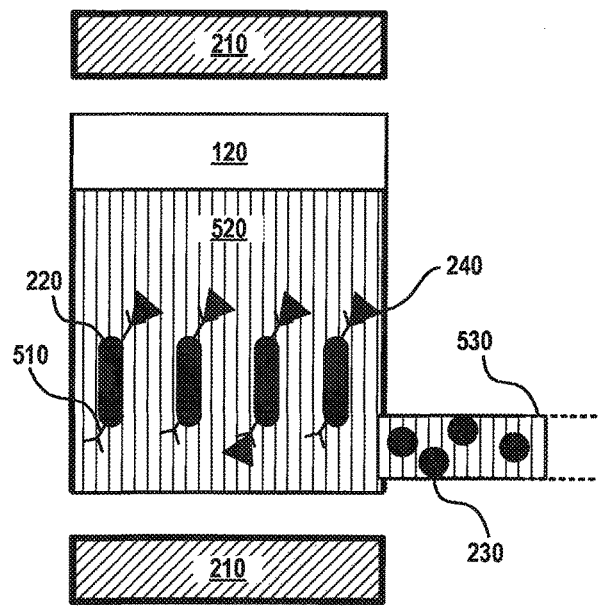

As depicted in FIG. 4C, the magnetic force generated by the magnet component 210 may be changed from a magnetic force that causes the elongated magnetic elements 220 to rotate to a magnetic force that immobilizes the elongated magnetic elements 220 within the processing vial 120. In FIG. 5D, therein is depicted a wash solution 520 being introduced into the processing vial 120 to wash away the fluid 110c and the non-target analytes 230, for example, to a waste reservoir 530. In this manner, the target analytes 240 may be captured and retained in the processing vial 120 for analysis and/or further processing. Although analytes 230, 240 and corresponding antibodies 510 have been used as an example in FIGS. 5A-D, embodiments are not so limited, as fluid separation may be carried out using any type of affinity-based components known to a person having ordinary skill in the art, such as through the use of other bio-reactive materials (e.g., phosphorescent compounds), magnetic affinity materials, and/or chemical affinity materials.

Figure 6A:
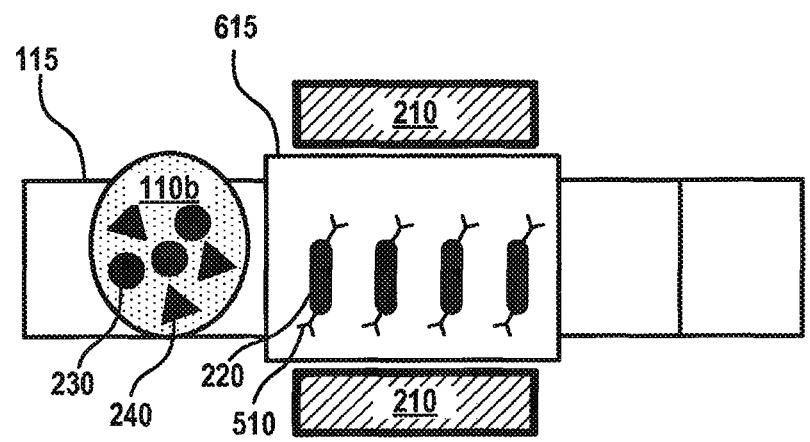
FIGS. 6A-C depict a flow diagram for fluid separation on the fluid surface of a microfluidic device according to various aspects of the applicant's teachings.
Figure 6B:
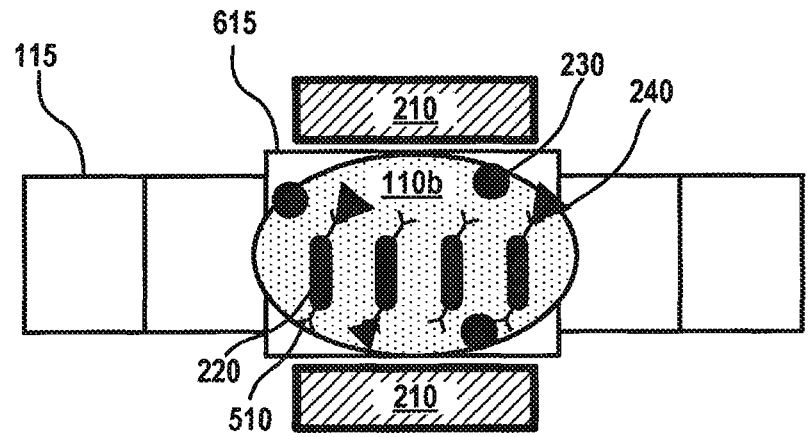
Figure 6C:
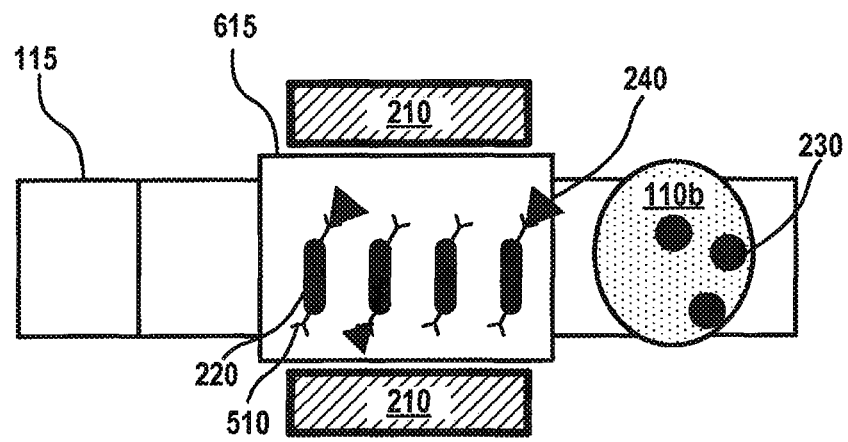

Although FIGS. 4A-D and 5A-D depict fluid mixing and separation within the processing vial 120, embodiments are not so limited, as fluid mixing and/or separation may be performed using the elongated magnetic elements 220 on any portion of the fluid surface 130. For instance, FIGS. 6A-C depict a flow diagram for fluid separation on the fluid surface 130 of the microfluidic device 100 according to various aspects of the applicant's teachings. In FIG. 6A, a volume of elongated magnetic elements 220 has been deposited onto a separation actuation electrode 615, which may be configured the same as the other actuation electrodes 115, but has been designated by the controller 125 as the electrode where separation will occur. A fluid 110b containing various analytes 230, 240 has been deposited on the array of actuation electrodes 115 and is being moved toward the separation electrode 615 through the application of appropriate voltages to the actuation electrodes 115 and the separation electrode 615. The elongated magnetic elements 220 have an affinity for certain analytes 230, 240, for instance, because the outer surface of the elongated magnetic elements 220 has been coated with antibodies 510 for a target analyte 240.

As shown in FIG. 6B, the fluid 110b may be combined with the volume of elongated magnetic elements 220 on the separation electrode 615. Due to the shape of the elongated magnetic elements 220, more surface area of the elongated magnetic elements 220 and, therefore, antibodies 510 may contact the fluid 110b and the analytes 230, 240 contained therein. In some embodiments, the magnet component 210 may be activated to provide a magnetic force that causes the elongated magnetic elements 220 to move (e.g., rotate and/or move laterally side-to-side) within the fluid 110b. The antibodies 510 may capture the target analyte 240 while the fluid 110b is located on the separation electrode 615. Referring to FIG. 6C, the magnet component 210 may be activated to immobilize the elongated magnetic elements 220 on the separation electrode 615. The actuation electrodes 115 may be activated to move the fluid 110b, and the non-targeted analytes 230 contained therein, away from the separation electrode 615. In this manner, the target analyte 240 may be separated from the fluid 110b and retained on the separation electrode 615 for analysis and/or further processing.

Figure 7A:
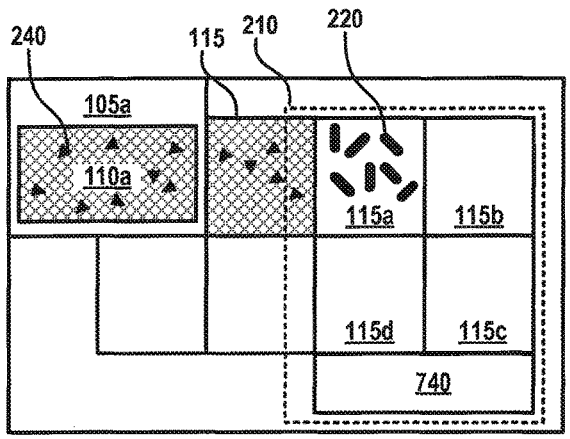
FIGS. 7A-F depict a flow diagram for fluid mixing and separation on the fluid surface of the microfluidic device according to various aspects of the applicant's teachings.
Figure 7B:
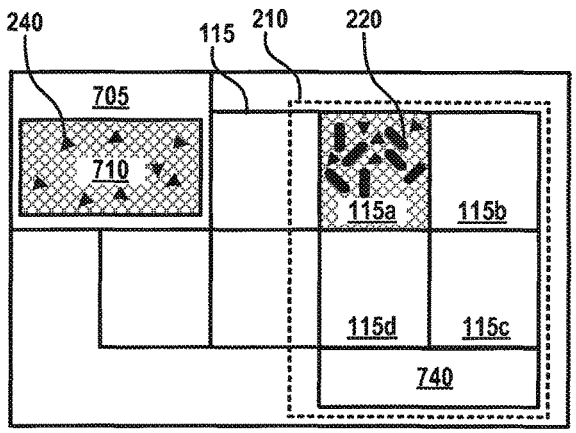
Figure 7C:
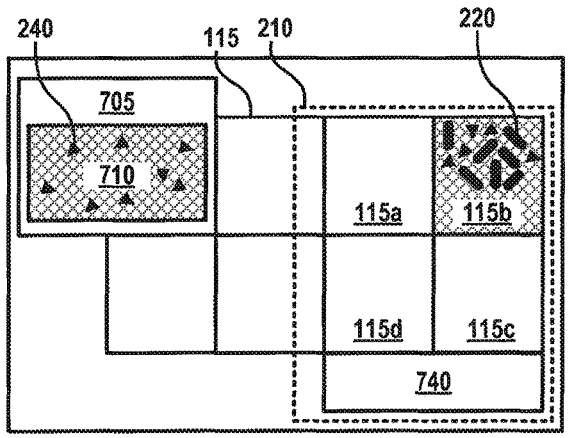
Figure 7D:
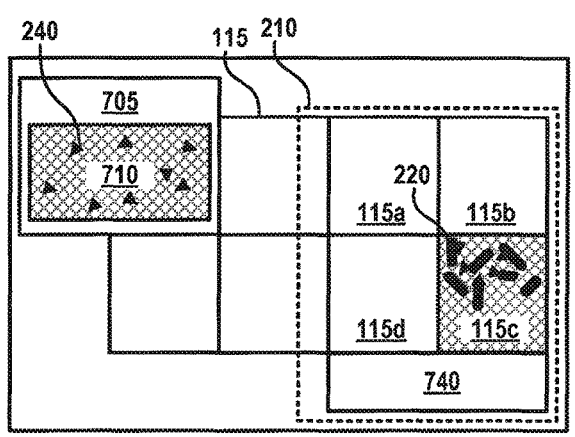
Figure 7E:
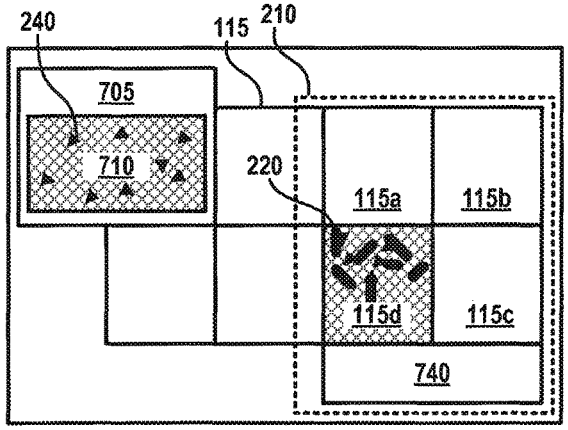
Figure 7F:
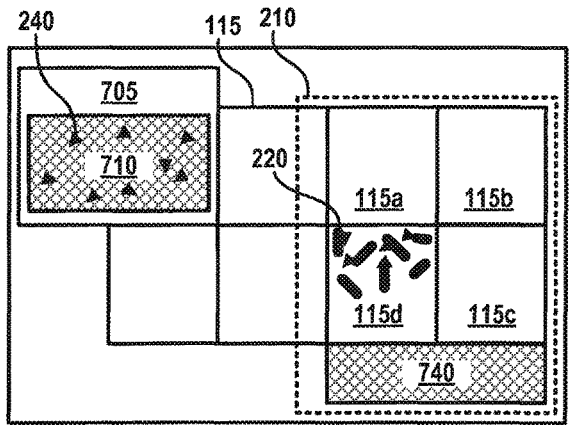

In another instance, FIGS. 7A-F depict a flow diagram for fluid mixing and separation on the fluid surface 130 of the microfluidic device 100 according to various aspects of the applicant's teachings. As shown in FIG. 7A, a unit of a fluid 110a containing a target analyte 240 may be deposited on an actuation electrode 115. A mixing area may be formed through actuation electrodes 115a-d. A first actuation electrode 115a within the mixing area may include elongated magnetic elements 220 having a binding affinity for the target analyte 240. Referring to FIG. 4B, the fluid 110a may be moved into the first actuation electrode 115a. As shown in FIGS. 4B-E, the mixture of elongated magnetic elements 220 and fluid 110a may be agitated by rotating the mixture through actuation electrodes 115a-d in a clockwise (or counterclockwise) motion. The sequence depicted in FIGS. 4B-E may be repeated to further agitate and mix the elongated magnetic elements 220 and the fluid 110a. As the elongated magnetic elements 220 and the fluid 110a are being agitated, the target analyte 240 are contacting and becoming bound to the elongated magnetic elements 220. In some embodiments, the magnet component 210 may be activated to provide a magnetic force that influences the motion of the elongated magnetic elements 220 within each of the actuation electrodes 115a-d. In this manner, the elongated magnetic elements 220 and the fluid 110a may be agitated through the motion of the elongated magnetic elements 220 within the fluid 110a and also through the movement of the elongated magnetic elements 220 and fluid 110a among actuation electrodes 115a-d. As shown in FIG. 7F, the magnet component 210 may be activated to immobilize the elongated magnetic elements 220 and a wash step may be implemented to wash the fluid 110a, and any non-targeted materials contained therein, from the actuation electrodes 115a-d.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. A digital microfluidic processing system, comprising:
   at least one fluid container having a plurality of elongated magnetic elements arranged therein, the fluid container being capable of receiving at least one fluid;
   a plurality of actuating electrodes that form a fluid surface that is positioned adjacent to the at least one fluid container such that fluids from the one fluid container are dispensable onto the fluid surface from the at least one fluid container;
   a magnet component positioned so as to generate a magnetic force within the fluid container sufficient to magnetically influence the plurality of elongated magnetic elements, the magnetic component comprising an assembly of magnets with a first portion of the assembly of magnets radially positioned at or substantially at a top portion of the at least one fluid container and a second portion of the assembly of magnets radially poisoned at or substantially at a bottom portion of the at least one fluid container; and
   a controller coupled to the magnet component that is capable of activating and deactivating the magnet components thereby controlling the magnetic field applied by the magnet component to the elongated magnetic elements to control movement thereof;
   wherein the magnetic force comprises a three-dimensional rotating magnetic force.

2. The system of claim 1, wherein the movement of the elongated magnetic elements causes a mixing of said at least one fluid.

3. The system of claim 1, wherein the elongated magnetic elements comprise a magnetic core and a non-magnetic coating.

4. The system of claim 3, wherein the magnetic core comprises at least one of $Fe_2O_3$ and $Fe_3O_4$.

5. The system of claim 1, wherein the at least one fluid comprises at least one target analyte and the plurality of elongated magnetic elements have an affinity for the at least one target analyte.

6. The system of claim 5, wherein the affinity is provided by antibodies selective for the at least one target analyte.

7. A method for processing a fluid, comprising:
   arranging a plurality of elongated magnetic elements within a fluid container in a digital microfluidic system;

positioning a plurality of actuating electrodes that form a fluid surface that is positioned adjacent to the fluid container such that fluids from the fluid container are dispensable onto the fluid surface from the fluid container positioning a magnet component to generate a magnetic force within the fluid container, wherein the magnetic force comprises a three-dimensional rotating magnetic force, the magnetic component comprising an assembly of magnets with a first portion of the assembly of magnets radially positioned at or substantially at a top portion of the fluid container and a second portion of the assembly of magnets radially poisoned at or substantially at a bottom portion of the fluid container;

receiving at least one fluid within the fluid container; and activating and deactivating the magnet component to generate the magnetic field within the fluid container sufficient to magnetically influence the plurality of elongated magnetic elements, thereby processing the at least one fluid.

8. The method of claim 7, further comprising transporting the processed at least one fluid to a measurement device for analysis.

9. The method of claim 8, wherein the measurement device comprises a mass spectrometer.

10. The method of claim 7, further comprising coating the plurality of elongated magnetic elements with an affinity material having an affinity for at least one target analyte in the at least one fluid.

11. The method of claim 10, wherein the affinity material comprises antibodies selective for the at least one target analyte.

12. The method of claim 11, further comprising performing fluid separation on the at least one fluid to capture the at least one target analyte.

* * * * *